United States Patent [19]

Hill

[11] 4,323,477
[45] Apr. 6, 1982

[54] ACID COPPER CHROMATE CONCENTRATES

[75] Inventor: Robert E. Hill, Webster Groves, Mo.

[73] Assignee: Koppers Company, Inc., Pittsburgh, Pa.

[21] Appl. No.: 81,396

[22] Filed: Oct. 3, 1979

[51] Int. Cl.³ ............................................. C09K 15/00
[52] U.S. Cl. .................................... 252/397; 424/140; 427/440; 106/15.05; 106/18.26
[58] Field of Search ......................... 252/397; 422/32; 427/288, 439, 440; 424/140; 148/6.2; 106/15.05, 18.26, 18.34

[56] References Cited

U.S. PATENT DOCUMENTS

| | | | |
|---|---|---|---|
| 3,948,802 | 4/1976 | Liddell | 252/397 |
| 3,957,494 | 5/1976 | Oberly | 424/140 |
| 4,218,249 | 8/1980 | Hill | 106/15.05 |
| 4,247,329 | 1/1981 | Mills | 424/140 |

*Primary Examiner*—Joseph L. Schofer
*Assistant Examiner*—J. L. Barr
*Attorney, Agent, or Firm*—Donald M. MacKay; Herbert J. Zeh, Jr.; Oscar B. Brumback

[57] ABSTRACT

An aqueous copper chromate concentrate substantially free of sulfate anions is provided which can be diluted for use as a wood preservative. The concentrate is formed of a hexavalent chromium compound, a bivalent copper compound, and an acid selected from nitric, sulfamic, fluosilicic, fluoboric and mixtures wherein the total oxide content of CuO and $CrO_3$ is from 25 to 60%.

13 Claims, No Drawings

ACID COPPER CHROMATE CONCENTRATES

BACKGROUND OF THE INVENTION

Acid copper chromate (ACC) wood preservatives are required by the American Wood Preservers Association Standard to have 31.8–28.0% copper as CuO and 68.2–63.3% hexavalent chromium as $CrO_3$. In addition, water soluble compounds used to make up the preservative must be bivalent copper, e.g. copper sulfate and hexavalent chromium, e.g. sodium or potassium dichromate and chromium trioxide.

ACC compositions are traditionally formulated with copper sulfate which is only moderately water soluble. Thus it is not feasible to form concentrates with copper sulfate containing formulations so as to obviate shipping excess water.

Accordingly, it is the object of this invention to provide novel wood preservatives which meet the AWPA Standard for ACC compositions but also can be formed in concentrates having from 25 to 60% total CuO and $CrO_3$ oxides. In addition, formulations are provided which, when diluted to the 0.8 to 14% level for application to wood, not only have the correct oxide ratio of from 1 part CuO to 2.145 $CrO_3$ to 1 part CuO to 2.161 $CrO_3$, but also have the proper pH of from 2.0 to 3.9 at 68°–77° F. when diluted to an aqueous solution of 15 to 22 grams of oxide per liter.

In contrast thereto, a liquid concentrate with copper sulfate and sodium dichromate dihydrate requires a reduction in total oxide content to 18% by weight for solubility down to 38° F.

DESCRIPTION OF THE INVENTION

The invention comprises three types of concentrate. The first is the salt type which is exemplified by sodium or potassium dichromate with cupric nitrate or the latter may be formed in situ with basic cupric carbonate and nitric acid. The salt type is characterized by having free cations other than copper.

A second type is the reacted type which is so characterized by having only copper cations. The reacted type is formed of acidic chromium trioxide with a bivalent copper compound selected from basic cupric carbonate, basic cupric hydroxide or cupric oxide and an acid selected from nitric, sulfamic, fluosilicic and fluoboric. The third type is a mixture of the above two types.

In formulating with both basic cupric carbonate and cupric oxide the powdered cupric compounds are added to the acid solution last with vigorous agitation. Basic cupric carbonate is added in increments to prevent the mixture from foaming over as carbon dioxide is released by the reaction. Basic cupric oxide is added in increments as it tends to form a cake.

The weight loss in the examples represents some water loss as vapor but is mostly due to carbon dioxide evolution. This loss is made up by adding back water at the end of the reaction which is fairly rapid and generally complete in 20–30 minutes.

Any method of treating wood with aqueous treating solutions can be used when wood is treated with the aqueous wood treating solutions of the invention. These methods include treating wood by injection of the solution under pressure in closed vessels or dipping in open vessels or by brush or spray painting of the solution.

The following examples will serve to illustrate the invention and preferred embodiments thereof. All parts and percentages in said examples and elsewhere in the specifications and claims are by weight unless otherwise specified.

EXAMPLES I AND II

The following concentrates were formulated by blending together the ingredients at room temperature with the exception that the cupric carbonate was added last and slowly with vigorous agitation.

| Ingredients | Percent by Weight | |
|---|---|---|
| | 1. | 2. |
| Sodium dichromate, dihydrate | 27.0 | 27.0 |
| Chromium trioxide | 2.4 | 2.4 |
| 70% Aqueous nitric acid | 1.5 | 22.3 |
| Basic cupric carbonate (55% Cu. min.) | — | 13.6 |
| Cupric nitrate, trihydrate | 29.0 | — |
| Distilled water | 40.0 | 37.5 |
| TOTAL | 100.0% | 102.8% |
| Wt. Loss | | −2.8% |
| | | 100.0% |

The 2.8% weight loss for Example II was caused by evolution of $CO_2$ and water vapor. Both examples had a total oxide content of 30% and a ratio of CuO to $CrO_3$ of 1 to 2.15. In addition, the concentrates were soluble down to 20°–10° F., and had a pH at 76° F. of 2.3 to 2.0, respectively, when diluted with water to an aqueous solution of 15 to 22 grams of oxide per liter.

EXAMPLE III

A 50% oxide concentrate was formed of 34.1% $CrO_3$, 23.1% copper carbonate (55% Cu. metal), 10% nitric acid (70% aqueous) and 37.8% distilled water. There was a weight loss of 5.0 grams per 105 grams of materials added upon formulation. The calculated $CrO_3$ content was 34.1 and the calculated copper oxide content 15.9 for a $CuO:CrO_3$ ratio of 1:2.145. The concentrate was liquid down to 0° F. with no precipitation and had a pH at 76° F. of 2.3 when diluted with water to an aqueous solution of 15 to 22 grams of oxide per liter.

EXAMPLE IV

A 55% oxide concentrate was formed of 37.61% chromium trioxide, 11% nitric acid (70% aqueous) and 31.68% distilled water to which was slowly added 25.41% basic cupric carbonate (55% Cu. minimum). There was a weight loss of 5.60% upon formulation due to the evolution of $CO_2$ and water vapor. The calculated $CrO_3$ content was 37.61% and the calculated copper oxide content 17.5% for a $CuO:CrO_3$ ratio of 1 to 2.14. The concentrate was stable down to 20° F. with no precipitation or crystallization and had a pH at 76° F. of 2.4 when diluted with water to an aqueous solution of 15 to 22 grams of oxide per liter.

EXAMPLE V

A 60% oxide concentrate was formed of 40.9% chromium trioxide, 12.0% nitric acid (70% aqueous) and 24.7% distilled water to which was slowly added 27.7% basic cupric carbonate (55% Cu. minimum). There was a weight loss of 5.3% upon formulation due to the evolution of $CO_2$ and water vapor. The calculated $CrO_3$ content was 40.9% and the calculated CuO content was 19.1% for a $CuO:CrO_3$ ratio of 1 to 2.14. The concentrate was stable down to 60° F. with no precipitation and had a pH at 76° F. of 2.1 when diluted with water to an aqueous solution of 15 to 22 grams of oxide per liter.

EXAMPLE VI

A 50% concentrate formulated with fluosilic acid was formed of 34.1% chromium trioxide, 23.1% basic cupric carbonate (55% Cu. minimum), 14.5% fluosilicic acid (30–32% aqueous), 5% nitric acid (70% aqueous) and 23.3% distilled water. The calculated $CrO_3$ content was 34.1% and the calculated CuO content was 15.9% for a $CuO:CrO_3$ ratio of 1:2.145. The concentrate was stable down to 10° F. with no precipitation or crystallization and had a pH at 76° F. of 2.35 when diluted with water to an aqueous solution of 15 to 22 grams of oxide per liter.

EXAMPLE VII

A 50% concentrate formulated with fluoboric acid was formed of 34.1% chromium trioxide, 23.1% basic cupric carbonate (55% Cu. minimum), 18.5% fluoboric acid (48% aqueous), 2% orthophosphoric acid (85% aqueous), and 22.3% distilled water. The calculated $CrO_3$ content was 34.1% and the calculated CuO content was 15.9% for a $CuO:CrO_3$ ratio of 1:2.145. The concentrate was stable down to 0° F. and had a pH of 2.2 at 76° F. when diluted with water to an aqueous solution of 15 to 22 grams of oxide per liter.

EXAMPLE VIII

A 40% concentrate formulated with sulfamic acid was formed of 27.4% chromium trioxide, 7.4% technical sulfamic acid prills, 50.9% distilled water and 18.2% basic cupric carbonate (55.9% Cu. by analysis). A loss occurred of 3.9 grams of the 103.9 grams original raw materials. The calculated $CrO_3$ content was 27.4% and the calculated CuO content was 12.7% for a $CuO:CrO_3$ ratio of 1 to 2.16. The concentrate was stable to 20° F. with no precipitation or cloudiness and had a pH at 76° F. of 2.1 when diluted with water to an aqueous solution of 15 to 22 grams of oxide per liter.

EXAMPLE IX

A 40% concentrate mixture was formed by mixing equal weights of the 30% oxide concentrate using sodium dichromate shown below as (A) and the 50% oxide using all chromium trioxide shown below as (B) to provide mixture (C).

| Ingredients | Percent by Weight | | |
|---|---|---|---|
| | (A) | (B) | (C) |
| Chromium trioxide | 2.4 | 34.1 | 18.3 |
| Sodium dichromate dihydrate | 27.0 | — | 13.6 |
| Basic cupric carbonate (55% Cu. min.) | 13.6 | 23.1 | 18.5 |
| 70% Aqueous nitric acid | 22.3 | 10.0 | 16.1 |
| Distilled water | 37.5 | 37.8 | 37.2 |
| TOTAL | 102.8 | 105.0 | 103.7 |
| Weight loss | −2.8 | −5.0 | −3.7 |

The concentrate was stable to 0° F. and had a pH of 2.1 at 76° F. when diluted with water to an aqueous solution of 15 to 22 grams of oxide per liter.

The composition of Example 8 was tested for fungicidal resistance by AWPA Standard M-10-77 method of testing wood preservatives by laboratory soil block cultures. Bio assay of weathered and unweathered treated southern pine blocks gave threshold values above 0.25 PCF oxides using Madison 698 (Poria Placenta) and 617 (Gleophyllum Traebum). The results using Madison 534 (Lentinus Lepideus) gave unweathered to weathered thresholds of less than 0.05 to 0.125 PCF.

EXAMPLE X

A 25% concentrate formulated with cupric sulfamate was formed of 22.5% sodium dichromate, dihydrate, 2% chromium trioxide, 11.3% basic cupric carbonate (55.9% Cu.), 20% technical sulfamic acid and 47.2% deionized water for a total of 103% and a 3% weight loss caused by evolution of $CO_2$ and water vapor. The concentrate had a CuO to $CrO_3$ ratio of 1:2.16, was stable at 10° F. after 9 days and only began to form a few crystals at 0° F. after 1 week (which were dissolved when allowed to warm to room temperature) and had a pH of 2.0 at 70° F. for an aqueous solution of 20 grams of oxide per liter.

The compositions of Examples 2,3,8,10 and a control composition were tested to determine the weight pickup and penetration of the waterborne oxide dilution into wood. The control composition was an 18% oxide copper sulfate liquid concentrate comprising 17.44% sodium dichromate, dihydrate, 18.05% cupric sulfate, pentahydrate, 0.61% chromium trioxide and 63.90% deionized water.

For the vacuum treatments four dry parallel grained southern pine sapwood specimens approximately ¾ by ¾ by 18 inches along the grain were weighed and their volumes calculated from micrometer measurements. Using these data the density of each specimen was determined in pounds per cubic foot of wood at the existing moisture content. The specimens were then sectioned across the grain into three inch blocks, with one specimen retained for oven dry moisture content to constant weight at 220° F.

Four preweighed blocks, one from each specimen, were used per treatment with one percent oxide aqueous dilutions of the indicated ACC concentrates. Inside a glass desiccator a vacuum of 25 to 26 inches of mercury was impressed for thirty minutes on each set of four blocks held vertically and weighted to prevent floating in the solutions, which were introduced under vacuum at room temperature. After releasing the vacuum the totally immersed blocks covered with a large excess of solution were allowed to stand at ambient conditions for two hours prior to removal for reweighing. Excess solution was removed by blotting with paper towels before weighing. From the individual weight increases the solution absorption was calculated in pounds per cubic foot of woods as follows:

| | Calculated Solution Absorption in Pounds per Cubic Foot of Wood from 1% Oxide Dilutions of: | | | | | |
|---|---|---|---|---|---|---|
| Parent Pine Specimen* Number | Density, PCF | % M.C. | Control | Ex. 2 | Ex. 3 | Ex. 8 | Ex. 10 |
| 1. | 33.9 | 7.3 | 40.6 | 40.7 | 38.6 | 38.8 | 39.8 |
| 2. | 33.9 | 7.5 | 40.5 | 40.9 | 40.4 | 38.7 | 41.0 |
| 3. | 33.0 | 7.0 | 43.4 | 38.6 | 41.8 | 39.6 | 40.7 |
| 4. | 35.4 | 7.4 | 40.0 | 38.4 | 39.8 | 38.0 | 39.7 |
| AVERAGE RETENTIONS | | | 41.1 | 39.7 | 40.2 | 38.8 | 40.3 |

*Density in pounds per cubic foot at percent moisture content based on oven dry weight of wood.

After four days of air drying at ambient temperature the surface color of all the treated blocks was light grayish brown. Each block was then split lengthwise along the grain and the depth of solution penetration determined visually by the residual color imparted by the oxides of the treating solutions. Regardless of the ACC composition all the test blocks were completely and uniformly penetrated. Qualititative color test reactions indicated the presence of both copper and chromium in the center of the treated blocks not indicated in the untreated oven dried replicates.

From the reported test, it was found that the copper and chromium salts penetrated the wood. Further, unlike powder concentrates which may be hazardous to the workers' health and require time to dissolve, the liquid concentrates are easily formulated without dust. In addition, the formulations containing fluorine and/or boron are found to provide enhanced preservative effectiveness.

What is claimed:

1. An aqueous copper chromate concentrate substantially free of sulfate anions formed of a hexavalent chromium compound selected from sodium dichromate, potassium dichromate, chromium trioxide and mixtures, a bivalent copper compound selected from basic cupric carbonate basic cupric hydroxide, cupric nitrate, cupric oxide and mixtures, and an acid selected from nitric, sulfamic, fluosilicic, fluoboric and mixtures wherein the total oxide content of CuO and $CrO_3$ is from 25 to 60% and the CuO to $CrO_3$ ratio is from 1 to 2.145 to 1 to 2.161.

2. The concentrate of claim 1 wherein the hexavalent chromium compound is chromium trioxide.

3. The concentrate of claim 1 wherein the acid is sulfamic acid.

4. The concentrate of claim 1 wherein the acid is fluosilicic acid.

5. The concentrate of claim 1 wherein the acid is fluoboric.

6. The concentrate of claim 1 wherein the acid is nitric.

7. An aqueous cellulose preservative solution substantially free of sulfate anions formed of a hexavalent chromium compound selected from sodium dichromate, potassim dischromate, chromium trioxide and mixtures, a bivalent copper compound selected from basic cupric carbonate, basic cupric hydroxide, cupric nitrate, cupric oxide and mixtures, and an acid selected from nitric, sulfamic, fluosilicic, fluoboric, and mixtures wherein the total oxide content of CuO and $CrO_3$ is from 0.8 to 14% and the CuO to $CrO_3$ ratio is from 1 to 2.145 to 1 to 2.161.

8. The solution of claim 7 wherein the hexavalent chromium compound is chromium trioxide.

9. The solution of claim 7 wherein the pH is from 2 to 3.9.

10. The solution of claim 7 wherein the acid is sulfamic acid.

11. The solution of claim 7 wherein the acid is fluosilicic acid.

12. The solution of claim 7 wherein the acid is fluoboric acid.

13. The solution of claim 7 wherein the acid is nitric acid.

* * * * *